(12) United States Patent
Pukki

(10) Patent No.: US 9,420,993 B2
(45) Date of Patent: Aug. 23, 2016

(54) CALIBRATION METHOD AND DEVICE TO BE CALIBRATED FOR MEASURING DENSITY OF A BONE

(75) Inventor: Jussi Pukki, Helsinki (FI)

(73) Assignee: Oscare Medical Oy, Vantaa (FI)

( * ) Notice: Subject to any disclaimer, the term of this patent is extended or adjusted under 35 U.S.C. 154(b) by 564 days.

(21) Appl. No.: 12/920,672

(22) PCT Filed: Feb. 17, 2009

(86) PCT No.: PCT/FI2009/050127
§ 371 (c)(1),
(2), (4) Date: Sep. 2, 2010

(87) PCT Pub. No.: WO2009/109696
PCT Pub. Date: Sep. 11, 2009

(65) Prior Publication Data
US 2011/0021910 A1    Jan. 27, 2011

(30) Foreign Application Priority Data
Mar. 5, 2008 (FI) .................................... 20085207

(51) Int. Cl.
*A61B 8/00* (2006.01)
*A61B 8/08* (2006.01)
*A61B 5/00* (2006.01)

(52) U.S. Cl.
CPC ............... *A61B 8/0875* (2013.01); *A61B 8/587* (2013.01); *A61B 5/4509* (2013.01); *A61B 2560/0252* (2013.01)

(58) Field of Classification Search
CPC ............ A61B 8/00; A61B 8/08; A61B 8/587; A61B 8/0875; A61B 5/4509
USPC .......................................... 600/438, 448, 449
See application file for complete search history.

(56) References Cited

U.S. PATENT DOCUMENTS

| 5,935,073 A | 8/1999 | Wilson et al. |
| 6,221,019 B1 | 4/2001 | Kantorovich |
| 7,112,173 B1 | 9/2006 | Kantorovich et al. |

FOREIGN PATENT DOCUMENTS

| EP | 1038501 A1 | 3/1993 |
| EP | 0585492 A1 | 3/1994 |

(Continued)

OTHER PUBLICATIONS

Bossy, Emmanuel et al., "Bidirectional Axial Transmission Can Improve Accuracy and Precision of Ultrasonic Velocity Measurement in Cortical Bone: A Validation on Test Materials", IEEE Transactions on Ultrasonics, Ferroelectrics, and Frequency Control, vol. 51, No. 1, Jan. 2004, pp. 71-79.
Supplemental European International Search Report, PCT/FI2009/050127 Critical Medical Oy, dated Sep. 27, 2011.
Piletskas, E.L., "Database WPI"; Section PQ; Week 8749; Derwent Publications Ltd.; AN 87-347489; XP-002085199; and SU 1 308 319 A; May 7, 1987, 1 page.

(Continued)

*Primary Examiner* — Joel Lamprecht
(74) *Attorney, Agent, or Firm* — McKee, Voorhees & Sease, PLC

(57) ABSTRACT

An ultrasound device can be calibrated for forming skeleton density information. This ultrasound device includes a calibration program integrated programmatically to the ultrasound device and a calibration part for calibrating a known distance L. The velocity of ultrasound is known for different temperatures in the calibration part. The ultrasound device includes at least two transmitters having a distance of L1 between them for transmitting ultrasound signals into the skeleton, and at least two receivers having a distance of L2 between them for receiving ultrasound signals from the skeleton. At least one of distances L1 and L2 is equal to the calibrated known distance L. The ultrasound device also includes a processing unit for calculating an ultrasound velocity in the skeleton.

5 Claims, 7 Drawing Sheets

(56) References Cited

FOREIGN PATENT DOCUMENTS

Figure 1:
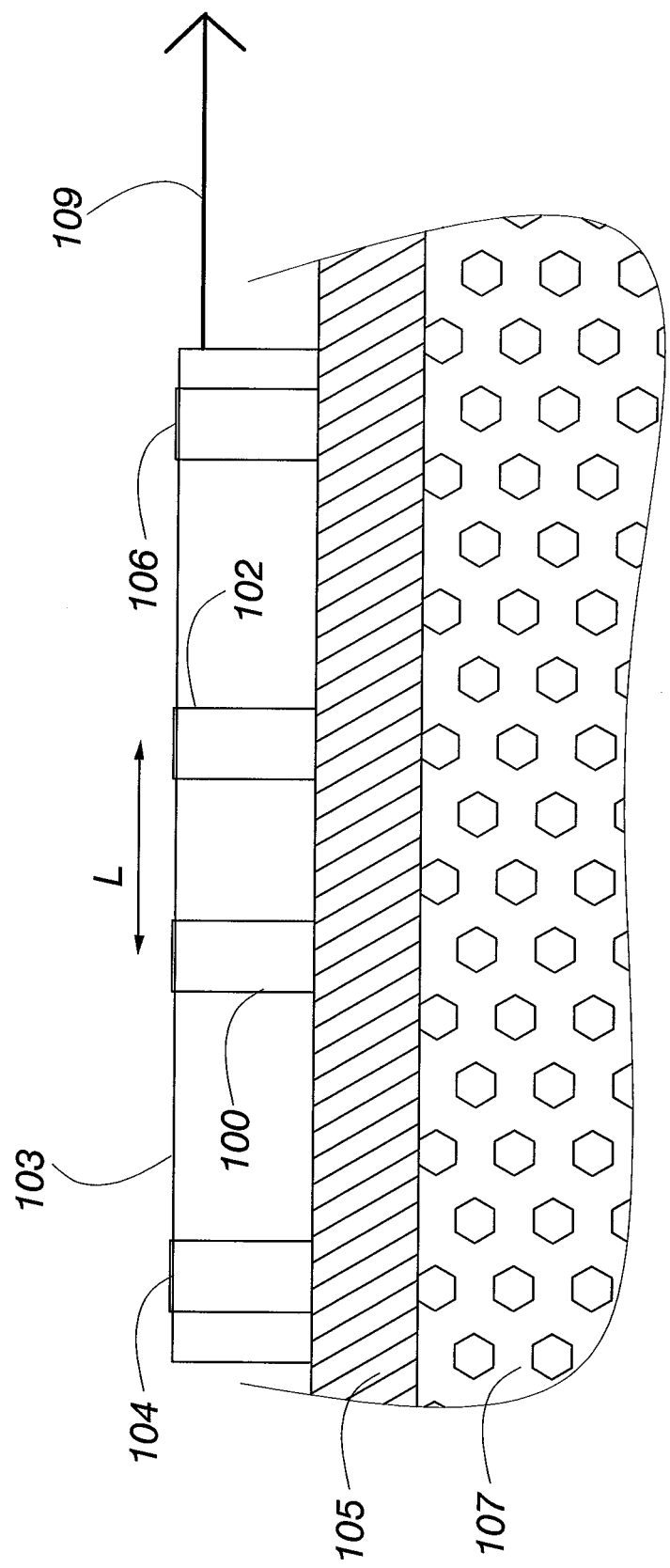

| | | |
|---|---|---|
| EP | 0 985 381 A2 | 3/2000 |
| EP | 1452138 A3 | 9/2004 |
| WO | WO 99/45348 A1 | 9/1999 |
| WO | WO 0024307 A2 | 5/2000 |
| WO | WO 0028316 A1 | 5/2000 |
| WO | WO 0028900 A1 | 5/2000 |
| WO | WO 03099132 A1 | 12/2003 |
| WO | WO 2008146204 A2 * | 12/2008 |

OTHER PUBLICATIONS

Shmakov, Y.E. "Database WPI"; Section PQ; Week 8909; Derwent Publications Ltd.; AN 89-067923; XP-002085200; and SU 1 420 383 A; Aug. 30, 1988, 1 page.

International Search Report, PCT/FI2009/050127, Critical Medical Oy, dated Jun. 10, 2009.

Finnish Office Action, FI 20085207, Critical Medical Oy, dated Jun. 8, 2009.

* cited by examiner

CALIBRATION METHOD AND DEVICE TO BE CALIBRATED FOR MEASURING DENSITY OF A BONE

THE FIELD OF THE INVENTION

Various reasons cause that bone density decreases and thus skeleton becomes weaker increasing a risk for different types of fractures. This phenomena is called osteoporosis.

THE PRIOR ART

Bone density is measured by measurement devices that measure the attenuation of x-rays that have penetrated through the bone. These devices are relatively expensive. Especially because of this reason more popular have become devices and methods that are based on the measurement of mechanical vibration, i.e. ultrasound, that propagates through the bone or on the surface of the bone.

In patent application publication EP1507476 A1 (CENTRE NAT RECH SCIENT) is presented an ultrasound measurement arrangement according to the prior art, where ultrasound is transmitted to the bone by using at least one transmitter and ultrasound is received by using several receivers and these receivers having not more that 1 cm distances among them. The determination of information on osteoporosis is based on formation of ultrasound spatial-time-frequency diagram by utilizing Fourier transformation or matrix calculation.

In publication EP1507476 A1 is told that an applicable frequency range is 100 kHz-5 MHz, but in practice transmitters and receivers presented in EP1507476 A1, that have not more than 0.5 cm distances between them, are not applicable below 1 MHz frequencies.

The formation of skeleton measurement results according to the prior art has as its biggest drawback that sufficient and trustworthy measurement results demand that at least ten, in practice much more, receivers are used to receive ultrasound signals. This increases much economical costs.

THE SHORT DESCRIPTION OF THE INVENTION

As an object of this invention is a method and a device utilizing said method to increase substantially accuracy in skeleton density measurements. This is achieved by an ultrasound device to be calibrated for forming skeleton density information. This ultrasound device comprises calibration arrangement comprising a calibration program integrated programmatically to the ultrasound device and a calibration part for calibrating a known distance L, and the velocity of ultrasound is known in different temperatures in said calibrating part. The ultrasound device comprises for forming skeleton density information at least two transmitters having a distance of L1 between them for transmitting ultrasound signals into the skeleton, at least two receivers having a distance of L2 between them for receiving ultrasound signals from the skeleton, as the calibrated known distance L at least one of distances L1 and L2 and a processing unit for calculating a ultrasound velocity in the skeleton for forming skeleton density information on the basis of the ultrasound signals received by said receivers by dividing known distance by an average of a travel time difference for a ultrasound signal between the receivers receiving said ultrasound signal from the first transmitter and a travel time difference for a ultrasound signal between the receivers receiving said ultrasound signal from the second transmitter.

An object of this invention is also a method for forming skeleton density information by calibration. In the method is performed a calibration measurement of distance L so that temperature of a calibrating part is measured, a travel time of the ultrasound is measured for the distance L to be calibrated in the calibrating part, and the distance L is calculated on the basis of the measured travel time and a known ultrasound velocity in the calibrating part in said temperature.

In the method skeleton density information is formed so that ultrasound signals are transmitted into the skeleton by at least two transmitters having a distance of L1 between them, ultrasound signals are received from the skeleton by at least two receivers having a distance of L2 between them, as the calibrated known distance L is at least one of distances L1 and L2 and a ultrasound velocity in the skeleton is calculated for forming skeleton density information on the basis of the ultrasound signals received by said receivers so that the known distance L is divided by an average of a travel time difference for a ultrasound signal between the receivers receiving said ultrasound signal from the first transmitter and a travel time difference for a ultrasound signal between the receivers receiving said ultrasound signal from the second transmitter.

In the bone density measurement according to the invention a propagation velocity of a ultrasound wave is measured, said ultrasound wave travelling on the surface of the bone or inside the bone travelling substantially along the direction of the surface of the bone, by succeeding to minimize problems existing in the prior art bone density measurement methods that are based on the ultrasound velocity measurements. The invention is preferable to accomplish at frequencies below 0.5 MHz and in the utilization of the invention is not needed a use of Fourier transform.

The invention is based on that a response data for the osteoporosis is determined on the basis of a velocity calculation for a ultrasound wave propagating along the fastest route through the soft tissue and the skeleton. In the method is used at least two transmitters locating in different locations for transmitting ultrasound signals into the skeleton and respectively the ultrasound signals are received from the skeleton by receivers locating in different locations, and the distance L between transmitters or receivers is known. The invention is further based on that temperature of a calibrating part is measured, a travel time of the ultrasound is measured for the distance L to be calibrated in the calibrating part, and the distance L is calculated on the basis of the measured travel time and a known ultrasound velocity in the calibrating part is said measured temperature. The calibrated distance information is utilized in the calculation of an ultrasound velocity in the skeleton for forming skeleton density information on the basis of the ultrasound signals received by said receivers so that the known distance is divided by a average of a travel time difference for a ultrasound signal between the receivers receiving said ultrasound signal from the first transmitter and a travel time difference for a ultrasound signal between the receivers receiving said ultrasound signal from the second transmitter.

The benefit of the invention is that with measurements, that are adjusted by utilizing calibrations, osteoporosis is detected reliably before it causes bone fractures, thus enabling prevention of osteoporosis by changing nutrients or by using medicines. When osteoporosis has been detected early enough, the risk for fractures can also be minimized by using different protection means.

LIST OF FIGURES

FIG. 1 presents a measure head according to the invention as placed on the skin for measurements.

Figure 2:
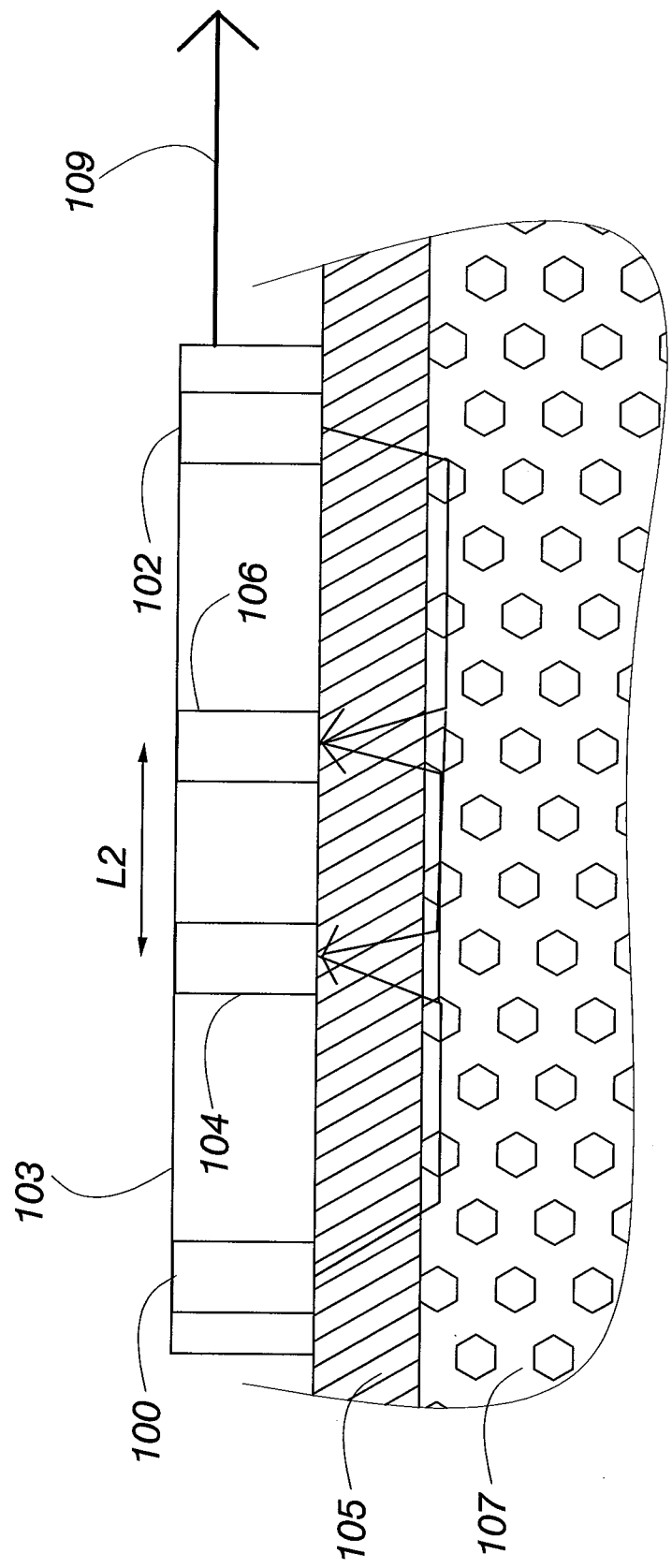

FIG. 2 presents a measurement according to the first preferred embodiment of the invention.

Figure 3:
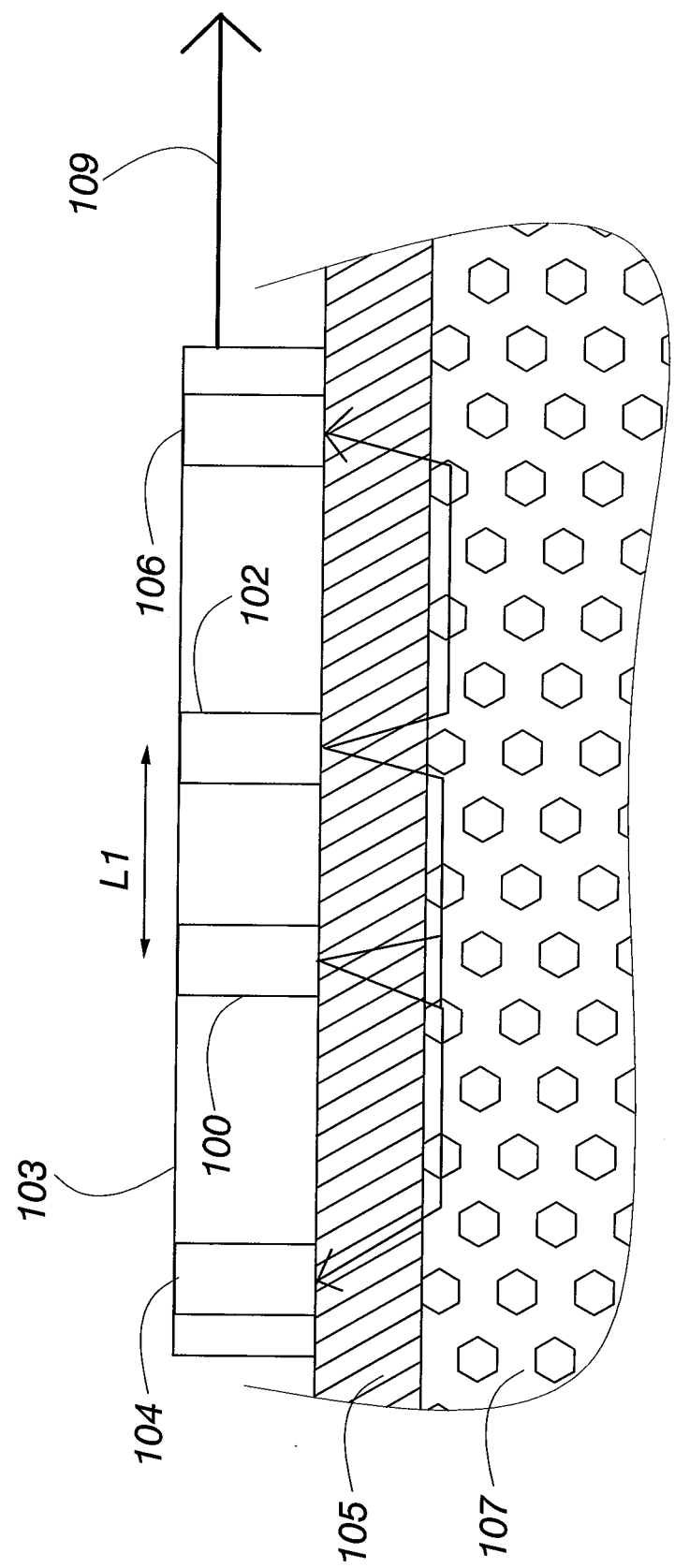

FIG. 3 presents a measurement according to the second preferred embodiment of the invention.

Figure 4A:
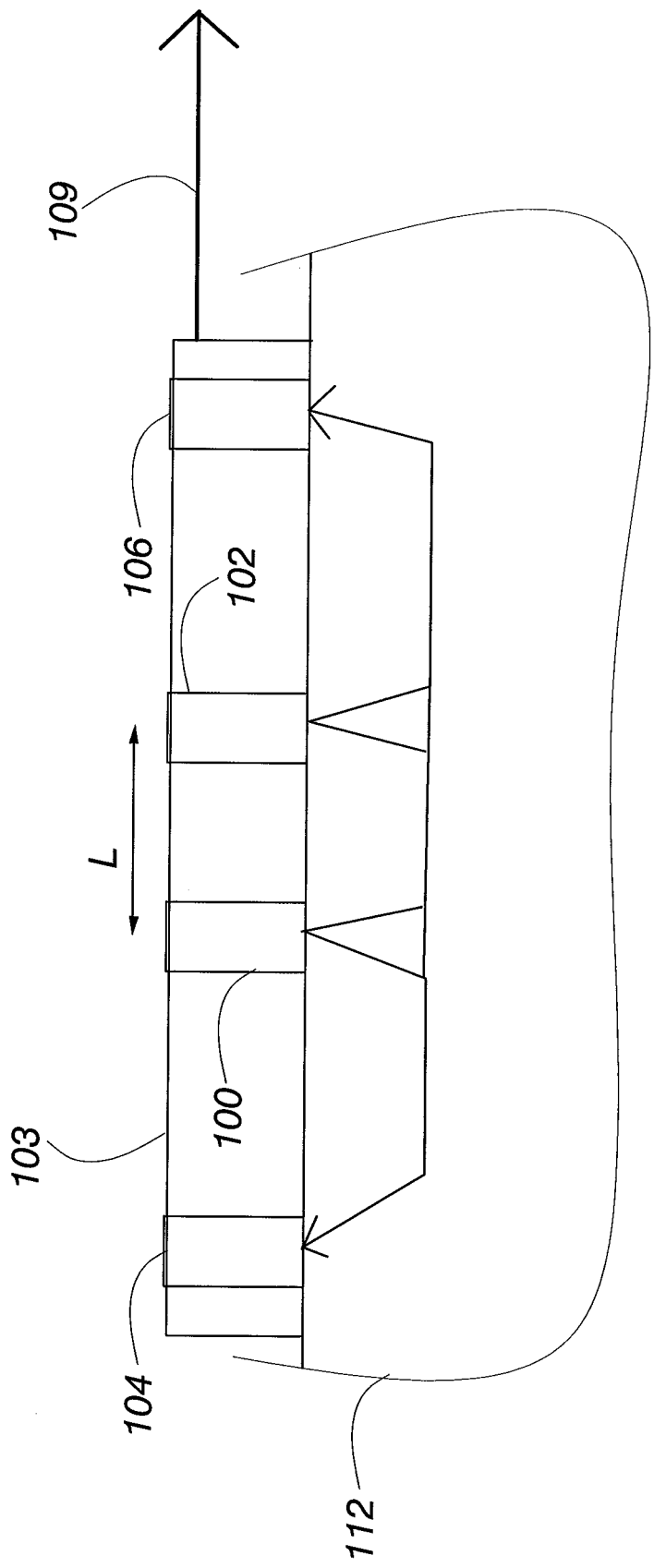
Figure 4B:
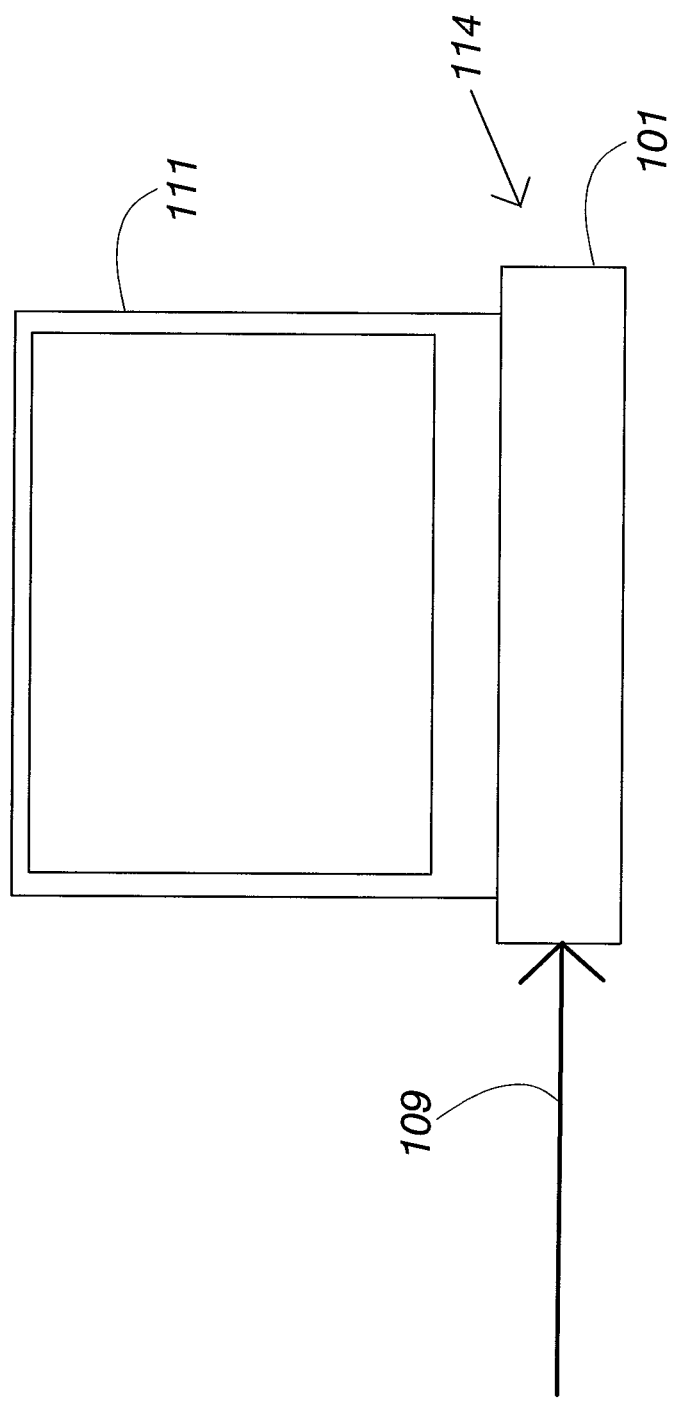

FIGS. 4A-4B present a calibrating arrangement for an ultrasound device according to the invention for calibrating a distance for known distances in different temperatures.

Figure 5A:
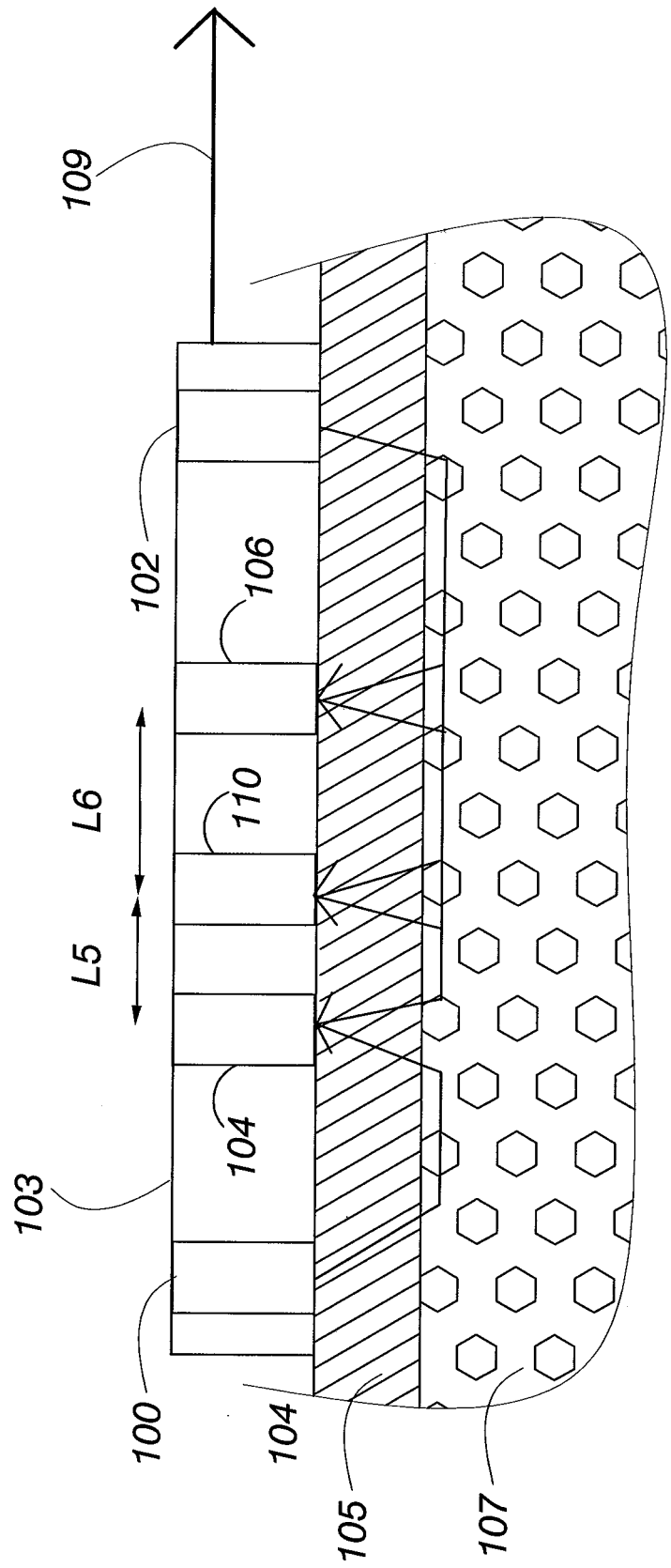
Figure 5B:
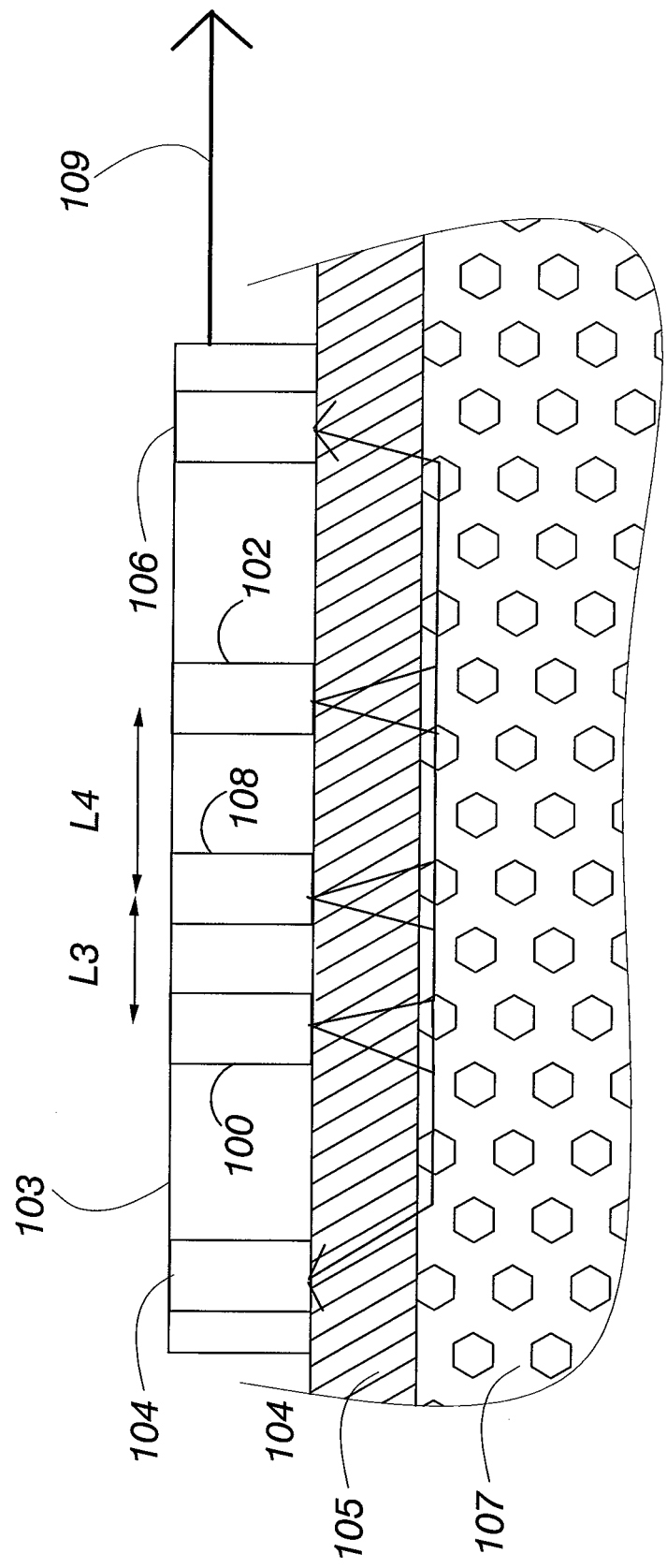

FIGS. 5A-5B present ultrasound devices according to the invention for researching the quality of ultrasound signals.

DETAILED DESCRIPTION OF THE INVENTION

An ultrasound wave can be described to be mechanical vibration propagating in a medium having different propagation characteristics in different mediums and their interfaces. When frequency of the ultrasound wave remains the same, velocity changes according to the composition of the medium.

In an embodiment according to the invention it can be enough that only two ultrasound sensors would be used, the first being a transmitter for transmitting ultrasound into the skeleton, and the second being a receiver for receiving ultrasound from the skeleton. In practice a soft tissue layer between the skeleton and sensor causes for measurements error factors depending on the different compositions and thicknesses that soft tissue layers have. Thus using of only two ultrasound sensors is often not enough to obtain acceptable measurement results in medicine.

The measure head of an ultrasound device according to the invention comprises at least four ultrasound sensors in row, of which at least two sensors are used for transmitting ultrasound signal into the patient and at least two are used for receiving ultrasound signal from the patient.

FIG. 1 presents a measure head according to the invention as placed on the skin for measurement. FIG. 1 presents as cross section soft tissue layer 105 and bone 107. The measure head comprises at least two transmitters 100, 102 for transmitting a ultrasound wave through soft tissue layer into the bone and at least two receivers 104, 106 for receiving the ultrasound wave from the bone through the soft tissue layer. From the measure head 103 is a wired or wireless data connection 109 to the processor unit 101 (FIG. 4B), that processes the measurement data received by the receivers.

In the first preferred embodiment of the invention presented in FIG. 2 the ultrasound device for forming skeleton density information comprises in the measure head 103 two transmitters 100, 102 for transmitting ultrasound signals into the skeleton. A distance L1 between said transmitters need not to be known. Ultrasound signals are received from the skeleton by receivers 104, 106 in the measure head 103 located so that they have a measured known distance L2 between them. The first travel time measurement of the ultrasound wave is performed so that the first transmitter sends at least one pulse shaped ultrasound wave signal through the soft tissue into the bone, where the ultrasound wave propagates on surface of the bone or inside the bone. When propagating on surface of the bone or inside the bone the ultrasound wave attenuates, and through the bone and soft tissue interface part of the ultrasound wave energy transfers to the soft issue. When the ultrasound wave arrives near the first receiver 104, part of the ultrasound wave energy transfers through the soft issue to the first receiver and the other part of the ultrasound wave propagates further. When the ultrasound wave arrives near the second receiver 106 locating further in the same direction as the first receiver, part of the ultrasound wave energy transfers through the soft issue to the second receiver and the other part of the ultrasound wave propagates again further.

If there would be no soft tissue, the ultrasound wave signal propagation velocity would be obtained by measuring the time that it takes for the signal to travel along the bone from the transmitter to the receiver, or alternatively from the first receiver to the second receiver, when the distance between them is known. In practical measurement the time for the signal to travel through the soft tissue is as its extent an unknown and positional factor affecting to the measurement result. When measuring time for the signal to travel between two receivers, a time for travel through the soft tissue would not cause error if the soft tissue would be equal and has same thickness at both receivers. Because in practical measurement the situation is not so, this causes error to the time measurement depending on the travel time differences through the soft issue at the receivers. In the embodiment according to the invention said error is eliminated so that a second travel time measurement for the ultrasound wave is performed by transmitting from a second transmitter 102 at least one pulse shaped ultrasound wave signal through the soft issue into the bone from a substantially opposite direction to the receivers 104, 106 as the described ultrasound wave signal sent from the first transmitter 100. Thus said ultrasound wave sent by the second transmitter 102 arrives first to the second transmitter 106 and after that to the first transmitter 104. The receivers 104, 106 receive the ultrasound signal sent by the second transmitter 102 in the similar way as they receive the ultrasound signal sent by the first transmitter 100 but timely in a different order.

In the described first and second travel time measurement a change, caused by the extraction between travel times through soft tissue layer, is the same, but with opposite signs, i.e. the absolute value is the same. The velocity of the ultrasound is calculated by dividing the known distance L2 between receivers 104, 106, i.e. the distance projected to the surface of the bone, by the average value of the measured time values in the first and second travel time measurement by this way eliminating the measurement error caused by the soft tissue layer. Distances from the transmitters 100, 102 to the receivers 104, 106 need not to be known, and the connection between the measure head 103 and soft tissue need not to be accurately adjusted.

The first preferred embodiment of the invention can be presented in equation form as follows:

$$V=2*L2/(|(tb0-t0)-(tc0-t0)|+|(tb1-t1)-(tc1-t1)|)=2*L2/(|tb0-tc0|+|tb1-tc1|),$$

where V=velocity of the ultrasound wave, L2 the known distance between receivers, t0=a transmittal time for the ultrasound signal sent from the first transmitter, t1=a transmittal time for the ultrasound signal sent from the second transmitter, tb0=a receiving time of the first receiver for the ultrasound signal sent from the first transmitter, tc0=a receiving time of the second receiver for the ultrasound signal sent from the first transmitter, tb1=a receiving time of the first receiver for the ultrasound signal sent from the second transmitter, and tc1=a receiving time of the second receiver for the ultrasound signal sent from the second transmitter.

The second preferred embodiment of the invention presented in FIG. 3 is much similar as the described first preferred embodiment of the invention, the main difference being, that the known distance needed in calculation is the known distance between transmitters 100, 102 that locates between receivers 104, 106. A distance L2 between said receivers 104, 106 need not to be known in the second preferred embodiment of the invention. As in the first preferred embodiment of the invention the transmitters and the receivers 104, 106 have been placed to the measure head 103 in row formation. The first travel time measurement of the ultrasound wave is performed so that the first transmitter sends at least one pulse shaped ultrasound wave signal through the soft tissue into the bone, where the ultrasound wave propagates on surface of the bone or inside the bone. When propagating on surface of the bone or inside the bone the ultrasound wave attenuates, and through the bone and soft tissue interface part of the ultrasound wave energy transfers to the soft issue. When the ultrasound wave arrives near the first receiver 104, part of the ultrasound wave energy transfers through the soft issue to the receiver 104. When the ultrasound wave arrives near the receiver 106 locating further in the opposite direction as the receiver 104, part of the ultrasound wave energy transfers through the soft issue to the receiver 106.

In the second preferred embodiment of the invention a second travel time measurement for the ultrasound wave is performed by transmitting from a second transmitter 102 at least one pulse shaped ultrasound wave signal through the soft issue into the bone where the ultrasound wave propagates on the surface of the bone or inside the bone. When the ultrasound wave arrives near the receiver 106, part of the ultrasound wave energy transfers through the soft issue to the receiver 106. When the ultrasound wave arrives near the receiver 104 locating further in the opposite direction as the receiver 104, part of the ultrasound wave energy transfers through the soft issue to the receiver 104. In the first and second travel time measurement a change, caused by the extraction between travel times through soft tissue layer, is the same, but with opposite signs, i.e. the absolute value is the same. The velocity of the ultrasound is calculated by dividing the known distance L1 between transmitters 100, 102, i.e. the distance projected to the surface of the bone, by the average value of the measured time values in the first and second travel time measurement by this way eliminating the measurement error caused by the soft tissue layer. Distances from the transmitters 100, 102 to the receivers 104, 106 need not to be known, and the connection between the measure head 103 and soft tissue need not to be accurately adjusted.

The second preferred embodiment of the invention can be presented in equation form as follows:

$$V=2*L1/(|(tb0-t0)-(tc0-t0)|+|(tb1-t1)-(tc1-t1)|)=2*L1/(|tb0-tc0|+|tb1-tc1|),$$

where V=velocity of the ultrasound wave, L1=the known distance between transmitters, t0=a transmittal time for the ultrasound signal sent from the first transmitter, t1=a transmittal time for the ultrasound signal sent from the second transmitter, tb0=a receiving time of the first receiver for the ultrasound signal sent from the first transmitter, tc0=a receiving time of the second receiver for the ultrasound signal sent from the first transmitter, tb1=a receiving time of the first receiver for the ultrasound signal sent from the second transmitter, and tc1=a receiving time of the second receiver for the ultrasound signal sent from the second transmitter.

In the first and second embodiment the ultrasound device comprise a processor unit 101 for forming density information of a skeleton by calculating ultrasound velocity in the skeleton on the basis of ultrasound signals received by the receivers 104, 106. To the processor unit 101, presented in FIG. 4B, is relayed via data connection 109 measurement data received by the receivers. The processor unit is a computer, or comparable, comprising a processor with a connection to a display unit 111, wherefrom processed measurement data can be researched, a keyboard, wherefrom can be given control and processing commands etc to the processor unit and via the processor unit to the whole ultrasound device. The processor unit 101 performs the calculation so that the known distance is divided by an average of a travel time difference for a ultrasound signal between the receivers 104, 106 receiving said ultrasound signal from the first transmitter 100 and a travel time difference for a ultrasound signal between the receivers receiving said ultrasound signal from the second transmitter 102. The electronics needed for processing measurement data can be located also elsewhere than in the processor unit 101, for example in the measure head 103. In the first preferred embodiment of the invention the known distance is the distance L2 between the receivers and in the second preferred embodiment of the invention the known distance is the distance L1 between the transmitters. In both embodiments the benefits of the invention are optimized when the known distance is at least one centimeter, but the invention can also used with shorter distances.

In the preferred embodiments of the invention the ultrasound device comprises transmitters 100, 102 for transmitting ultrasound signals into the skeleton with different transmitters 100, 102 at different time moments.

As transmitters 100, 102 can be used multi frequency transmitters for forming different frequencies for the ultrasound signals in different skeleton density measurement situations. Also as receivers 104, 106 can be used multi frequency receivers for receiving said ultrasound signals comprising different frequencies in different skeleton density measurement situations. These bone density measurements performed by using different frequencies give information on skeleton density complementary to each other in an object to be researched. In the preferred embodiments transmitters 100, 102 transmit 100-500 kHz frequencies ultrasound signals into the skeleton and the receivers 104, 106 receives 100-500 kHz frequencies ultrasound signals from the skeleton.

In FIGS. 4A-4B is presented a calibrating arrangement for an ultrasound device according to the invention. In the first and second preferred embodiment of the invention the measure head 103 is made so that transmitters 100, 102 and receivers 104, 106 are fixed to the measure head steadily so that relative positions between them remains same.

During the production of the measure head the temperature of the calibrating part 112 is measured and a travel time of the ultrasound is measured for the distance L to be calibrated in the calibrating part and after that the distance L is calculated on the basis of the measured travel time and a known ultrasound velocity in the calibrating part 112 in said temperature by multiplying the travel time and the velocity. In the first preferred embodiment of the invention the calibration is performed for the distance L2 and in the second preferred embodiment of the invention for the distance L1.

In the calibration measurement can be used a calibrating part 112 comprising material that simulates bone, such as for example plastics. The calibrating part 112 can be delivered to an ultrasound device user together with the calibration arrangement and with it can also be performed checking calibrations during the use of the ultrasound device.

A calibration program is integrated programmatically to the processor of the processor unit 101 (FIG. 4B) as a part of the calibration arrangement that is delivered together with the ultrasound device, which arrangement can also comprise said calibrating part 112 needed in the production phase of the measure head for calibrating a distance L for known distances in different temperatures. When performing bone density measurement according to the invention, temperature T is also measured and on the basis of the measured temperature the calibration program calculates an accurate information on the known distance L, that is used for calculating ultrasound velocity in the bone by using calibration for more accurate forming of bone density information.

FIG. 5A presents ultrasound device according to the first preferred embodiment of the invention for researching the quality of ultrasound signals, that ultrasound device comprises in the measure head 103 for researching the quality of ultrasound signals at least one receiver 110 for receiving ultrasound signals from the skeleton, that receiver locates at the known distance L5 from the first receiver 104 and at a known distance L6 from the second receiver 106 between the first 100 and the second 102 transmitter. The known distance L2 is the distance between receivers 104, 106 as presented in FIG. 2. As connected to the first preferred embodiment of the invention the receiver 110 receives ultrasound signals transmitted from a first direction by the transmitter 100 and from the opposite direction
ultrasound signals transmitted by the transmitter 102 together with receivers 104, 106, and on the basis of the received signals is calculated ultrasound velocities at the known distances L2, L5, L6. If it is noticed that ultrasound velocities at the known distances L2, L5, L6 are clearly different, or some velocity value can even not be measured, it can noted that some ultrasound sensor does not have a proper contact on the surface of the skin or some ultrasound sensor is broken. A considerable difference between velocities can be for example 5%, but it can also be much less or much more. By this way the user can be taught to make the measurement position of the sensor better and a service alarm operation can be performed that alarms automatically when the measure head 103 needs a control checking or service.

FIG. 5B present ultrasound device according to the second preferred embodiment of the invention for researching the quality of ultrasound signals, that ultrasound device comprises in the measure head 103 for researching the quality of ultrasound signals at least one transmitter 108 for transmitting ultrasound signals into the skeleton, that transmitter 108 locates at the known distance L3 from the first transmitter 100 and at a known distance L4 from the second transmitter 102 between the first 104 and the second 106 receiver. The known distance L1 is the distance between transmitters 100, 102 as presented in FIG. 3. Signals transmitted by each transmitter in turn are received with the receivers 104, 106, and on the basis of the received signals is calculated sound velocity values at known distances L1, L3, L4. If it is noticed that ultrasound velocities at the distances L1, L3, L4 are clearly different, for example 5%, or some velocity value can even not be measured, it can noted that some ultrasound sensor does not have a proper contact on the surface of the skin or some ultrasound sensor is broken. A considerable difference between velocities can be for example 5%, but it can also be much less or much more. By this way the user can be taught to make the measurement position of the sensor better and a service alarm operation can be performed that alarms automatically when the measure head 103 needs a control checking or service.

Related to FIG. 5A the quality checking operation can be performed in a more developed manner by using burst-like ultrasound, in which the first wave having the highest velocity is lower than the second wave. Velocity of the ultrasound is measured by receiving with receivers 104, 106 and 110 by using the known distances L5, L6 and L2 as described with the first preferred embodiment (FIG. 2). If it is noticed that ultrasound velocities at the distances L1, L3, L4 are clearly different, for example 5%, or some velocity value can even not be measured, it can noted that some receiver or transmitter does not have a proper contact on the surface of the skin or some receiver or transmitter is broken. This is caused for example by that a receiver, having a bad contact on the skin, has not been able to receive the first low wave and/or a transmitter, having a bad contact, has transmitted only very low ultrasound wave. A considerable difference between velocities can be for example 5%, but it can also be much less or much more.

Correspondingly related to FIG. 5B velocity of the ultrasound is measured by receiving with receivers 104, 106 ultrasound transmitted with transmitters 100, 102 and 108 by using the known distances L3, L4 and L1 as described with the second preferred embodiment (FIG. 3) of the invention. If it is noticed that velocities of the ultrasound received by the receivers are clearly different, for example 5%, it can noted that some receiver does not have a proper contact on the surface of the skin or some receiver is broken. This is caused for example by that a receiver, having a bad contact on the skin, has not been able to receive the first low wave and/or a transmitter, having a bad contact, has transmitted only very low ultrasound wave. A considerable difference between velocities can be for example 5%, but it can also be much less or much more.

The invention claimed is:

1. An ultrasound device to be calibrated for determining osteoporosis, comprising:
    for determining osteoporosis two transmitters (100, 102) having the calibrated fixed known distance of L1 between them for transmitting ultrasound signals into the skeleton;
    two receivers (104, 106) for receiving said ultrasound signals from the skeleton; said transmitters (100, 102) transmitting ultrasound signals of frequencies below 250 kHz into the skeleton and said receivers (104, 106) receiving ultrasound signals of frequencies below 250 kHz from the skeleton; and
    electronics needed for processing measurement data is located in at least one location of a processor unit (101) and of a measure head (103) for calculating an ultrasound velocity in the skeleton for determining osteoporosis on the basis of the ultrasound signals received by said receivers (104, 106)), which signals have travelled over said known distance L1 from opposite directions to eliminate soft tissue effects, by dividing said known distance L1 by an average of a travel time difference for an ultrasound signal between the receivers (104, 106) receiving said ultrasound signal from the first transmitter (100) and a travel time difference for an ultrasound signal between the receivers (104, 106) receiving said ultrasound signal from the second transmitter (102);
    a calibration arrangement consisting of a calibration program (114) integrated programmatically to the ultrasound device and a calibrating part (112) for calibrating a known distance L1 and means for measuring a temperature T of the calibrating part, and the velocity of ultrasound is known in different temperatures in said calibrating part (112) based on a previous calibration performed using known references; and
    wherein based on the measured temperature T and average travel time over said known distance L1 from opposite directions to eliminate soft tissue effects, said average travel time being calculated on the basis of measured travel time differences, the calibration program is adapted to calculate accurate information on the known distance L1 by utilizing known velocity of ultrasound at the measured temperature T.

2. The ultrasound device according to claim 1, wherein said transmitters (100, 102) transmit ultrasound signals into the skeleton at different moments in time.

3. A method for determining osteoporosis by calibration, comprising:
measuring a temperature T of a calibrating part (112);
calculating travel time of ultrasound for the distance L1 to be calibrated on the basis of travel time differences in the calibrating part (112) of signals which have travelled over said known distance L1 from opposite directions to eliminate soft tissue effects;
performing a calibration measurement of distance L1 so that temperature of a calibrating part (112) is measured, a travel time of the ultrasound is measured for the distance L1 to be calibrated in the calibrating part (112), and the calibrated distance L1 is calculated on the basis of the measured travel time and a known ultrasound velocity in the calibrating part (112) in said measured temperature, the velocity of ultrasound being known in different temperatures in said calibrating part (112) on the basis of previous calibration performed by using known references;
determining osteoporosis so that ultrasound signals are transmitted into the skeleton by two transmitters (100, 102) having the calibrated fixed known distance of L1 between them, ultrasound signals are received from the skeleton by two receivers (104, 106), which signals have travelled over said known distance L1 from opposite directions to eliminate soft tissue effects, said transmitters (100, 102) transmitting ultrasound signals of frequencies below 250 kHz into the skeleton and said receivers (104, 106) receiving ultrasound signals of frequencies below 250 kHz from the skeleton; and
an ultrasound velocity in the skeleton is calculated for determining osteoporosis by using electronics located in at least one location of a processor unit (101) and of a measure head (103) on the basis of the ultrasound signals received by said receivers (104, 106) so that said known distance L1 is divided by an average of a travel time difference for an ultrasound signal between the receivers (104, 106) receiving said ultrasound signal from the first transmitter (100) and a travel time difference for an ultrasound signal between the receivers (104, 106) receiving said ultrasound signal from the second transmitter (102).

4. The method according to claim 3, wherein said ultrasound signals are transmitted into the skeleton with different transmitters 100, 102 at different time moments.

5. The method according to claim 3, wherein the distance L1 is the only known distance used in calculating the ultrasound velocity in the skeleton.

\* \* \* \* \*